(12) United States Patent
McIntosh (10) Patent No.: US 8,246,601 B2
(45) Date of Patent: Aug. 21, 2012

(54) METHODS FOR INTRAVASCULAR ENGRAFTMENT IN HEART

(75) Inventor: Charles L. McIntosh, Silver Spring, MD (US)

(73) Assignee: Cook Medical Technologies LLC, Bloomington, IN (US)

( * ) Notice: Subject to any disclaimer, the term of this patent is extended or adjusted under 35 U.S.C. 154(b) by 824 days.

(21) Appl. No.: 12/034,186

(22) Filed: Feb. 20, 2008

(65) Prior Publication Data
US 2008/0200899 A1 Aug. 21, 2008

Related U.S. Application Data

(60) Provisional application No. 60/902,739, filed on Feb. 21, 2007.

(51) Int. Cl.
*A61M 31/00* (2006.01)
(52) U.S. Cl. .......... 604/522; 604/507; 604/508
(58) Field of Classification Search .......... 604/507, 604/508, 522; 606/7
See application file for complete search history.

(56) References Cited

U.S. PATENT DOCUMENTS

| | | | |
|---|---|---|---|
| 5,130,141 A | 7/1992 | Law et al. | |
| 5,328,470 A | 7/1994 | Nabel et al. | |
| 5,476,453 A * | 12/1995 | Mehta ............... | 604/532 |
| 5,486,359 A | 1/1996 | Caplan et al. | |
| 5,543,318 A | 8/1996 | Smith et al. | |
| 5,580,779 A | 12/1996 | Smith et al. | |
| 5,693,622 A | 12/1997 | Wolff et al. | |
| 5,698,531 A | 12/1997 | Nabel et al. | |
| 5,707,969 A | 1/1998 | Nabel et al. | |
| 6,090,622 A | 7/2000 | Gearhart et al. | |
| 6,235,000 B1 | 5/2001 | Milo et al. | |
| 6,245,566 B1 | 6/2001 | Gearhart et al. | |
| 6,297,220 B1 | 10/2001 | Leiden et al. | |
| 6,436,907 B1 | 8/2002 | Leiden et al. | |
| 6,481,439 B1 * | 11/2002 | Lewis et al. ............... | 128/898 |
| 6,514,217 B1 | 2/2003 | Selmon et al. | |
| 6,579,302 B2 | 6/2003 | Duerig et al. | |
| 6,719,725 B2 | 4/2004 | Milo et al. | |
| 2002/0098167 A1 | 7/2002 | Anversa | |
| 2002/0110910 A1 | 8/2002 | Gwathmey et al. | |
| 2003/0009190 A1 * | 1/2003 | Kletschka et al. .......... | 606/200 |
| 2004/0048375 A1 | 3/2004 | Alt | |
| 2004/0230219 A1 | 11/2004 | Roucher | |
| 2005/0119679 A1 | 6/2005 | Rabiner et al. | |

(Continued)

OTHER PUBLICATIONS

Freyman T., et al., "A Quantitative, Randomized Study Evaluating Three Methods of Mesenchymal Stem Cell Delivery Following Myocardial Infarction," *European Heart Journal Advance Access*, 27:1114-1122 (2006).

(Continued)

*Primary Examiner* — Kevin C Sirmons
*Assistant Examiner* — Emily Schmidt
(74) *Attorney, Agent, or Firm* — Brinks Hofer Gilson & Lione (57) ABSTRACT

The invention relates to a method of engrafting donor cells into injured myocardium. The method includes delivering donor cells to a delivery site adjacent to and downstream of a chronic total occlusion and treating the chronic total occlusion. The delivery device may be a catheter with a wireguide that may be provided by a retrograde approach via an unoccluded artery or antegrade approach through the chronic total occlusion. The invention also relates to a method of treating injured myocardium and cell compositions for treatment of injured myocardium.

19 Claims, 7 Drawing Sheets

U.S. PATENT DOCUMENTS

| | | | |
|---|---|---|---|
| 2005/0171478 A1 | 8/2005 | Selmon et al. | |
| 2005/0187607 A1* | 8/2005 | Akhtar et al. | 623/1.15 |
| 2006/0015126 A1* | 1/2006 | Sher | 606/159 |
| 2006/0069346 A1 | 3/2006 | Smith et al. | |
| 2006/0083720 A1 | 4/2006 | Fraser | |
| 2006/0263339 A1* | 11/2006 | Poznansky et al. | 424/93.7 |
| 2007/0154555 A1* | 7/2007 | Strauss et al. | 424/486 |

OTHER PUBLICATIONS

Jain, M., et al., "Cell Therapy Attenuates Deleterious Ventricular Remodeling and Improves Cardiac Performance After Myocardial Infarction," *Circulation*, 103:1920-1927 (2001).

Oron U., et al., "Technical Delivery of Myogenic Cells Through an Endocardial Injection Catheter for Myocardial Cell Implantation," *Int J Cardiovasc Intervent.*, 3:227-230 (2000).

Perin E.C. and Lopez J., "Methods of Stem Cell Delivery in Cardiac Diseases," *Nature Clinical Practice Cardiovascular Medicine*, 3(1):S110-S113 (2006).

Pouzet, B., et al., "Intramyocardial Transplantation of Autologous Myoblasts," *Circulation*, 102:(III):III-210-III-215 (2000).

Sherman, W., et al., "Catheter-Based Delivery of Cells to the Heart," *Nature Clinical Practice Cardiovascular Medicine*, 3(1):S57-S64 (2006).

Suzuki, K., et al., "Cell Transplantation for the Treatment of Acute Myocardial Infarction Using Vascular Endothelial Growth Factor-Expressing Skeletal Myoblasts," *Circulation*, 104(Suppl. I):I-207-I-212 (2001).

Zimmerman, W.H., et al., "Tissue Engineering of a Differentiated Cardiac Muscle Construct," *Circulation Res.*, 90:223-230 (2002).

International Search Report for PCT Application No. PCT/US2008/002152.

\* cited by examiner

METHODS FOR INTRAVASCULAR ENGRAFTMENT IN HEART

RELATED APPLICATIONS

The present patent document claims the benefit of the filing date under 35 U.S.C. §119(e) of Provisional U.S. Patent Application Ser. No. 60/902,739, filed Feb. 21, 2007, which is hereby incorporated by reference.

BACKGROUND

1. Technical Field

The present invention relates to methods, compositions and devices for intravascular engraftment in heart and other organs.

2. Background Information

Cardiovascular disease includes dysfunctional conditions of the heart, arteries, and veins that supply oxygen to vital life-sustaining areas of the body like the brain, the heart itself, and other vital organs. Lack of oxygen can result in tissue or organ death. Common forms of cardiovascular disease include heart disease and stroke, the first and third leading causes of death for both men and women in the United States, accounting for approximately forty percent of all deaths. About sixty-one million Americans have some form of cardiovascular disease, with about 650,000 Americans dying of cardiovascular disease each year.

Vascular occlusions, such as chronic total occlusions (CTOs), are leading contributors of various vascular diseases, including but not limited to, cardiovascular disease, vascular disease, peripheral artery disease and artherosclerosis.

A CTO in a vasculature of a body and especially peripheral vascular and coronary arteries has life or limb threatening effects for a patient. A CTO is a condition in which the occluding material substantially blocks the cross section of the vasculature over a variable length of the vasculature. The CTO substantially stops blood flow through the vasculature and can result in oxygen deprivation to the tissue near the occlusion. The CTOs can occur throughout the arterial system of the body. Because the coronary arteries, classified as "end circulation," represent the only source of blood supply to the myocardium, i.e., cardiac muscle cells, the blockage of these vessels can be especially critical.

Although numerous methods and devices, including devices that push through the occlusion to open the vessel (see for example, U.S. Pat. No. 6,579,302) and devices that cross a total occlusion in a blood vessel (see for example, U.S. Pat. No. 6,235,000), have been proposed to treat CTOs, these devices or methods only address the issue of re-establishing oxygenated blood flow to the underperfused viable tissue or non-viable tissue that may have resulted from the limited supply or lack of oxygen due to the CTO.

To date, some methods of treating damaged myocardium have been proposed. For example, one method includes providing pharmaceutical therapies in an effort to restore heart function. However, such therapies may not be particularly effective if the damage to the heart is too severe, and pharmaceutical therapy is not believed to regenerate cardiomyocytes, but instead acts to block or promote certain molecular pathways that are thought to be associated with the progression of heart disease to heart failure.

Another method includes "cell therapy." Cell therapy involves the administration of endogenous, autologous and/or or nonautologous cells to a patient. For example, myogenic cells can be injected into damaged cardiac tissue with the intent of replacing damaged heart muscle or improving the mechanical properties of the damaged region.

There are several strategies for cell delivery in cardiac cell therapy. The cells can be delivered through coronary arteries or coronary veins. Alternatively, direct intramyocardial injection can be performed, using a surgical, transendocardial, or transvenous approach. See for example, Sherman W., et al., "Catheter-based delivery of cells to the heart," *Nature Clinical Practice Cardiovascular Medicine* (2006) 3, S57-S64; Perin E. C. and Lopez J., "Methods of stem cell delivery in cardiac diseases," *Nature Clinical Practice Cardiovascular Medicine* (2006) 3, S110-S113; Freyman T., et al., "A Quantitative, Randomized Study Evaluating Three Methods of Mesenchymal Stem Cell Delivery Following Myocardial Infarction," *European Heart Journal Advance Access* (2006) 27(9), 1114-1122; and Oron U., et al., "Technical Delivery of Myogenic Cells Through an Endocardial Injection Catheter for Myocardial Cell Implantation," *Int J Cardiovasc Intervent*. (2000) 3(4), 227-230.

There are, however, some limitations to such cell therapies. For example, one limitation of seeding the myocardium with intravascular (coronary artery) injection is that the coronary flow though the area seeded with cells; the transplanted cells can be washed downstream before a significant or desired number of cells could establish or engraft themselves in the area of injured myocardium. In addition, the current cell therapies are not localized to the diseased target area and allow for systemic spill over and potential for side effects. Accordingly, there is need in the art for enhanced efficacy of cell therapies and methods and therapies that would allow localized delivery of the cells to the treatment area. This localized delivery will then allow the cells to engraft, divide and establish themselves and function at the site of implantation.

SUMMARY

In one embodiment, the invention relates to a method of engrafting donor cells into injured myocardium. The method includes the steps of delivering donor cells to a delivery site adjacent to and downstream of a chronic total occlusion and later ablating the chronic total occlusion to establish oxygenated blood supply to the donor cells. The method may further include allowing the donor cells a time sufficient to engraft, divide and establish themselves at the delivery site. The time sufficient to implant and establish the donor cells at the delivery site may be from about 7 days to about 14 days. The time sufficient to implant and establish the donor cells at the delivery site may be about 14 days. Preferably, the donor cells may be delivered to the delivery site via a delivery device, such as a catheter or a microcatheter or other suitable device. In some instances, the delivery device approaches the delivery site through an un-occluded coronary artery. The delivery device may approach the delivery site through a retrograde approach. Alternatively, the delivery device may approach the delivery site through an antegrade approach. The delivery device may also approach the delivery site through a partial opening of the chronic total occlusion. In some instances, simultaneous right and left coronary arteriograms may be performed to show arterial connections. The donor cells may be myocytes, including ventricular myocytes; stem cells (e.g., adult stem cells or embryonic stem cells); or other progenitor cells (e.g., multipotent adult progenitor cells). The donor cell may also include other types of cells, such as skeletal muscle derived cells, skeletal muscle cells, skeletal myoblasts, cardiac derived cells, bone marrow-derived cells, mesenchymal cells, stromal cells, smooth muscle cells, fibroblasts, pluripotent cells, totipotent cells, hematopoietic stem cells, cells from cord blood, and isolated CD34+ cells. The method may further include a step of delivering a composition comprising the donor cells and optionally at least one agent that enhances donor cell engraftment, survival, proliferation and differentiation. The composition may also optionally include at least one carrier, excipient or diluent. A biocompatible marker may also be delivered. In some instances, in the step of delivering, about $10^2$ to about $10^{10}$ donor cells may be delivered. The donor cells may be delivered about 2 centimeters from the chronic total occlusion. The method may further include delivering a stent or other medical device. The stent or other device may be adapted to release a therapeutic agent at the delivery site.

In another embodiment, the invention relates to a method of treating injured myocardium. The method includes delivering donor cells to a delivery site adjacent to and downstream of a chronic total occlusion; and ablating the chronic total occlusion to establish blood supply to the donor cells.

In yet another embodiment, the invention relates to a method of engrafting donor cells into injured myocardium. The method includes delivering donor cells to a delivery site adjacent to and downstream of a chronic total occlusion; delivering an agent that enhance donor cell engraftment, survival, proliferation and differentiation; and ablating the chronic total occlusion to establish blood supply to the donor cells.

DETAILED DESCRIPTION OF THE DRAWINGS AND THE PRESENTLY PREFERRED EMBODIMENTS

In the following detailed description, reference is made to the accompanying drawings which form a part hereof, and in which is shown by way of illustration some specific embodiments in which the invention may be practiced. These embodiments are described in sufficient detail to enable those skilled in the art to practice the invention, and it is to be understood that the embodiments may be combined, or that other embodiments may be utilized and that structural and logical may be made without departing from the spirit and scope of the present invention. The following detailed description provides examples, and the scope of the present invention is defined by the appended claims and their equivalents.

I. Overview

The invention is based on the unexpected discovery by the inventor that the area adjacent to and downstream of a vascular inclusion, such as a chronic total occlusion (CTO), which is supplied by collateral vessels, is a low flow area suitable for effective implantation or engraftment of donor cells, such as myocytes, stem cells or other progenitor cells. This low flow area contains hybernating myocardium, scar myocardium, and/or a mix of hybernating myocardium and scar myocardium. The inventor discovered that the low flow area provides favorable conditions to engraft cells by allowing for longer dwell time so that the cells delivered to the area could engraft, divide and establish themselves prior to re-establishing oxygenated blood supply to the area. Because this is a low flow area, the cells are not washed away from the delivery and implantation site by the coronary flow. As a result, the cells are able to seed the small coronary and collateral vessels and establish themselves at the delivery site. Once these cells are established (about 2 weeks), the CTO may be treated antegrade or retrograde, for example by ablating the CTO using known methods and devices, and coronary blood flow restored. This procedure restores blood flow to the injured myocardium (viable and non-viable) and the new engrafted cells.

In one embodiment, the invention relates to a method of engrafting donor cells into injured myocardium. The method includes delivering donor cells, such as myocytes, stem cells, or other progenitor cells described in more detail below, to a delivery site (i.e., the low flow area) adjacent to and downstream of a CTO. In some instances, the donor cells are delivered within about 2 cm from the CTO. The donor cells are preferably delivered to underperfused areas. The donor cells may be delivered to the delivery site via a delivery device, such as a catheter or microcatheter or other suitable delivery device. The method further may include allowing the donor cells a time sufficient to engraft, divide and establish themselves at the delivery site and ultimately establish viable functioning myocardium. After allowing some time sufficient for the donor cells to engraft, divide and establish themselves at the delivery site, the CTO may be treated, for example by ablating or other methods. The CTOs may be approached either antegrade or retrograde to establish blood flow to the downstream myocardium as described in more detail below.

In another embodiment, the method may further include delivering a bare metal or a drug eluting stent, a stent graft or other suitable medical device following the procedure. The method may also include delivering a drug via a balloon catheter or the like.

II. Definitions

It should be noted that references to "an", "one", or "various" embodiments in this disclosure are not necessarily to the same embodiment, and such references contemplate more than one embodiment.

The terms "vascular occlusion(s)," "chronic total occlusion(s)" and "CTO(s)" as used herein refer to a collection of a matter including, but not limited to, intravascular blood clots, thrombus, plaque, fibrocalcific plaque, biological material, fibrin, calcified plaque, calcium deposits, occlusional deposits, atherosclerotic plaque, fatty deposits, adipose tissues, atherosclerotic cholesterol buildup, fibrous material buildup, platelets, cellular debris, and other occlusive materials that substantially blocks the cross section of the vasculature over a variable length of the vasculature, including the coronary arteries. Pathologically, the major component of the CTO is fibrocalcific plaque. The density of the proximal and distal "cap" of the plaque may be of different hardness.

The term "vasculature" as used herein refers to the entire circulatory system for the blood supply including the venous system, the arterial system and the associated vessels, arteries, arterioles, capillaries, veins, blood, and the heart. The arterial system is the means by which blood with oxygen and nutrients is transported to tissues. The venous system is the means by which blood with carbon dioxide and metabolic by-products is transported for clearance by the lungs, liver and kidneys.

The right and left ventricles of the heart are divided by the septum. The "septal perforators" arise from the left anterior descending artery and pass into the septum where they supply blood to the septal myocardium and conduction tissues. Septal perforators may also connect to the right coronary artery via the posterior descending artery. Septal perforators can vary in number and size.

The term "ablate" as used herein refers to removing, clearing, destroying or taking away a CTO. "Ablation" as used herein refers to a removal, partial opening (for antegrade approach), clearance, destruction, or taking away of the CTO. All these terms may be used interchangeably.

As used herein "somatic stem cell" or "stem cell" or "hematopoietic cell" refers to either autologous or allogenic stem cells, which are unspecialized (undifferentiated) cells that are characteristically of the same family type (lineage). Stem cells retain the ability to divide throughout life and give rise to cells that can become highly specialized and take the place of cells that die or are lost. Stem cells contribute to the body's ability to renew and repair its tissues. Unlike mature cells, which are permanently committed to their fate, stem cells can both renew themselves as well as create new cells of whatever tissue they belong to (and other tissues). Stem cells may be obtained from the bone marrow, peripheral blood, or other sources.

As used herein, the term "adult stem cells" refers to stem cells that are not embryonic in origin nor derived from embryos or fetal tissue.

The term "progenitor cells" refers to precursor stem cells that are unspecialized or have partial characteristics of specialized cells that are capable of undergoing cell division.

The term "myocytes" refers to cardiac muscle cells.

The term "damaged myocardium" or "injured myocardium" refers to myocardial cells which have been exposed to ischemic conditions secondary to partial or complete obstruction of coronary arteries supplying oxygenated blood to these myocardial cells. These ischemic conditions may have been caused by a CTO, acute coronary syndrome (ACS), partial occlusions, myocardial infarction, or other cardiovascular disease or related complaint. In this application, the damaged myocardium resulted from a CTO. The damaged myocardium includes hybernating myocardium (viable tissue) and scar myocardium (non-viable tissue; the lack of oxygen causes the death of the cells in the surrounding area, leaving an infarct, which will eventually scar).

The term "hybernating myocardium" refers to myocardial cells which are viable but underperfused due to, for example, a CTO. The cells may be kept viable via, for example, collateral vessels. The condition may be potentially reversible after revascularization.

The term "scar myocardium" refers to a transition area often associated with hybernating myocardium, of non-viable cells that do not contract that resulted from the lack of oxygen.

As used herein, "assemble" refers to the assembly of differentiated somatic stem cells into functional structures i.e., myocardium and/or myocardial cells, coronary arteries, arterioles, and capillaries etc. This assembly provides functionality to the differentiated myocardium and/or myocardial cells, coronary arteries, arterioles and capillaries.

The term "catheter" refers to a tube that is inserted into a blood vessel to access the vessel. Catheter includes catheter per se, or a catheter set including a catheter, needle, wireguide, introducer sheath and other suitable medical devices. Catheter may be a microcatheter.

The term "low flow area" refers to an area having lower than the "average coronary blood flow" through the area. The low flow area may have blood flow as low as about 0 to about 2 milliliters (mL) per minute and will depend on the number of collateral vessels to the area. This low flow area is located adjacent to and downstream from the CTO.

The term "average coronary blood flow" refers to the coronary blood flow in subjects that do not have vascular occlusions in the coronary arteries. The coronary blood flow in a subject without coronary CTOs depends on numerous factors, such as the weight of the subject, and can vary from up to 250 mL per minute.

The term "proximal" refers to an area nearer to a point of reference such as an origin or a point of attachment. In this application the term proximal refers to an area nearer to the origin of either the left or right coronary arteries.

The term "distal" refers to an area downstream from the chronic total occlusion.

The term "retrograde" refers to movement opposite the blood flow.

The term "antegrade" refers to movement in the direction of the blood flow.

As used herein, "patient" or "subject" may encompass any vertebrate including but not limited to humans, mammals, reptiles, amphibians and fish. However, advantageously, the patient is a mammal such as a human, or an animal mammal such as a domesticated mammal, e.g., dog, cat, horse, and the like, or production mammal, e.g., cow, sheep, pig, and the like.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning described in U.S. Patent law and the term is open-ended, allowing for the presence of more than that which is recited so long as basic or novel characteristics of that which is recited is not changed by the presence of more than that which is recited, but excludes prior art embodiments.

III. The Coronary System

Figure 1:
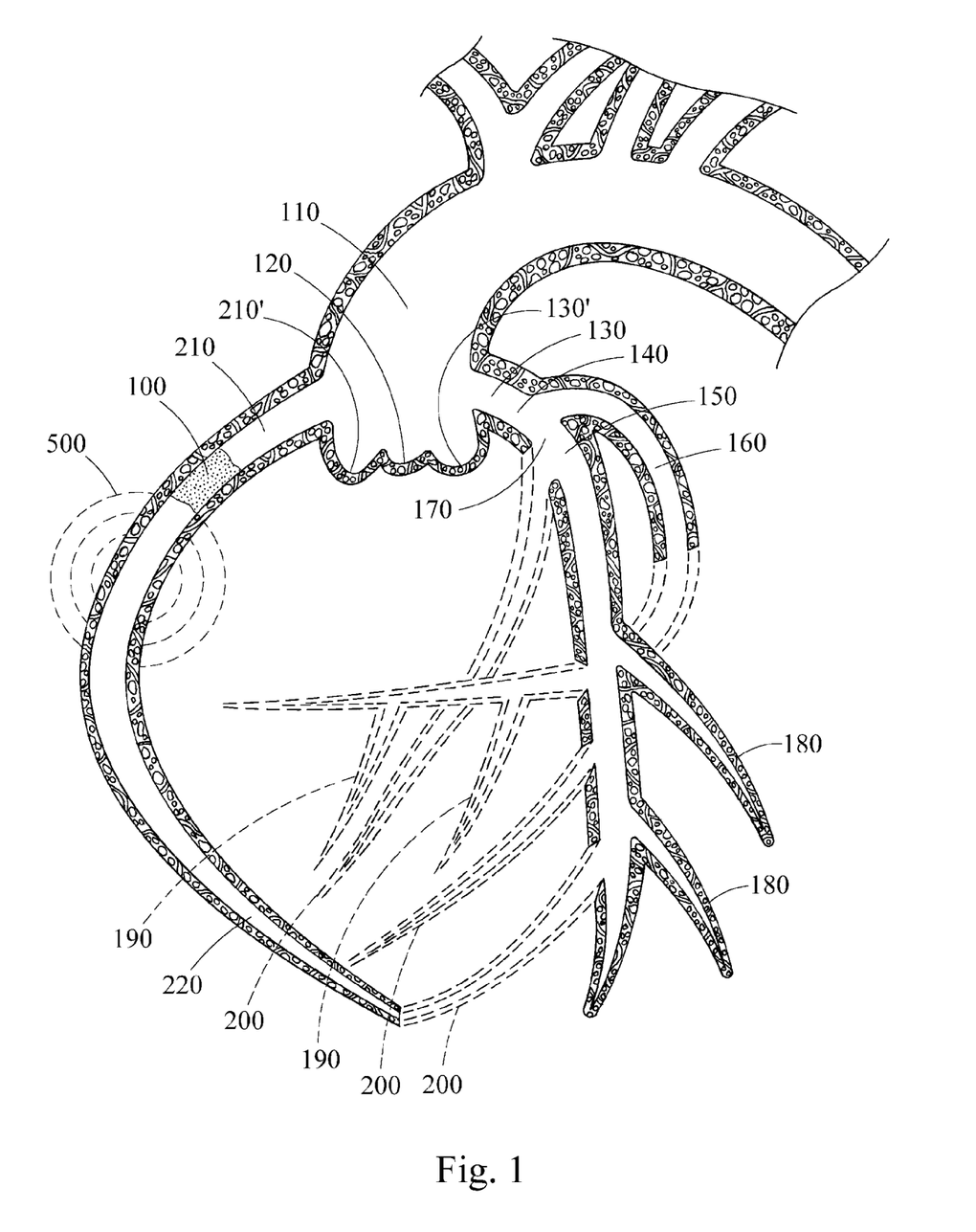
FIG. 1 is a schematic illustration of the coronary system and chronic total occlusion.

The heart, shown in FIG. 1, is supplied by two main blood vessels, which are the two coronary arteries, left coronary artery 130 and right coronary artery 210, that originate from the ascending aorta 110. The two coronary arteries 130, 210 arise near the commencement of the aorta 110 immediately above the attached margins of the aortic valve 120.

The right coronary artery 210 arises from the right coronary cusp 210'. It passes at first between the conus arteriosus and the right auricula and then runs in the right portion of the coronary sulcus, coursing at first from the left to right and then on the diaphragmatic surface of the heart from right to left as far as the posterior longitudinal sulcus, down which it is continued to the apex of the heart as the posterior descending branch 220 in a right dominant system. It gives off a large marginal branch which follows the acute margin of the heart and supplies branches to both surfaces of the right ventricle. It also gives twigs to the right atrium and to the part of the left ventricle which adjoins the posterior longitudinal sulcus.

The left coronary artery 130, larger than the right, arises from the left coronary cusp 130' as the left main 140 and divides into a left anterior descending 150 and a circumflex branch 160. The left anterior descending branch 150 passes at first behind the pulmonary artery and then comes forward between that vessel and the left auricula to reach the anterior longitudinal sulcus, along which it descends to the incisura apicis cordis; it gives branches to both ventricles and interventricular septum. The circumflex branch follows the left part of the coronary sulcus, running first to the left and then to the right, reaching nearly as far as the posterior longitudinal sulcus; it gives branches to the left atrium and ventricle via the obtuse marginal branches 190. In some cases, there is a free anastomosis between the minute branches of the two coronary arteries in the substance of the heart.

As previously discussed, in cardiovascular disease, the coronary arteries may become totally occluded resulting in CTOs 100.

As further illustrated in FIG. 1, the CTO 100 may block the entire cross section of the right coronary artery 210. The CTOs 100 may be comprised of many materials which build up along the inner diameter of the coronary artery 210 and build inward to substantially reduce the cross section of the coronary artery 210. As the CTOs 100 builds, the blood flow through the artery decreases and may eventually stop. An area of hybernating myocardium and associated scar myocardium 500 may form as a result.

The CTO 100 blocks the flow of blood through the coronary artery 210. Like all organs and tissues in the body, the heart muscle needs oxygen rich blood to survive. Blood is supplied to the left and right coronary arteries 130 and 210, respectively, by the aorta 110, the main blood supplier to the body. As discussed above, the left coronary artery 130 and the right coronary artery 210 subsequently branch off into smaller arteries, which supply oxygen rich blood to the entire heart muscle. The right coronary artery 210, which branches into proximal right coronary artery, SA branch, right ventricular branch, and posterior descending coronary artery 220 in about 70% of people supplies blood to the right side of the heart, which subsequently pumps blood to the lungs. The left coronary artery 130, as the left main 140 branches into the left anterior descending artery 150, diagonal branches 180, septal perforators 200, circumflex artery 160, and the obtuse marginal branches 190 supplies blood to the left side of the heart, which subsequently pumps blood to the rest of the body, as discussed above. By blocking the flow of blood through the coronary arteries, the CTO 100 poses a life threatening condition. In certain patients, however, collateral vessels may compensate for obstructed coronary arteries and lack of blood supply to the heart, although flow through the collateral vessels is limited.

Collateral vessels can play a significant role in supplying oxygen to an organ, particularly when oxygen delivery is limited by disease in the normal vasculature. Collateral vessels can be pre-existing vessels that normally have little or no blood flow. Acute or chronic occlusion of normal vessels (e.g., CTO of coronary artery, thrombosis of a large artery) can cause a redistribution of pressures within the vascular bed thereby causing blood flow to occur in collateral vessels. Conditions of chronic stress (e.g., endurance exercise training or chronic hypoxia) can also cause new blood vessels to form by angiogenesis.

Collateral blood vessels are particularly important in the coronary and skeletal muscle circulations. In the heart, collateral vessels can help to supply blood flow to ischemic regions due to stenosis or occlusion of epicardial arteries (i.e., coronary arteries that run on the surface of the heart). Collateral vessels can become more numerous as a coronary artery develops progressive stenosis and ultimately total occlusion. Collateral blood flow may be an important mechanism in limiting infarct size in the heart.

For example, if the CTO 100 occurs in main right coronary artery 200, left-to-right collateral vessels (i.e., collateral vessels from the left to the right coronary artery) or right-to-right collateral vessels (i.e., collateral vessels from the right coronary artery upstream from the occlusion to the right coronary artery downstream from the occlusion) may form to supply blood to myocardium downstream from the CTO. If the CTO occurs in the left coronary artery (not shown), right-to-left collateral vessels (i.e., collateral vessels from the right to left coronary artery) or left-to-left collateral vessels (i.e., collateral vessels from the left coronary artery upstream from the occlusion to the left coronary artery downstream from the occlusion) may form to supply blood to myocardium downstream from the CTO. Blood flow from the collateral vessels, although limited, allows to maintain the myocardial tissue alive resulting in a viable myocardial tissue, i.e., hybernating myocardium. Some non-viable tissue, i.e., scar myocardium, may also be present even though collateral vessels were formed. However, if collateral vessels do not form, a non-viable scar tissue of the myocardium may develop.

IV. Method of Engrafting Donor Cells

In one embodiment, the invention relates to a method of engrafting donor cells into injured myocardium. The method is preferably a method of engrafting donor cells into injured myocardium due to a chronic total occlusion in a coronary artery. The method includes the steps of:

delivering donor cells to a delivery site adjacent to and downstream of a CTO (i.e., the low flow area); and later ablating the CTO.

The method may further include locating the CTO and the damaged myocardial tissue near the area adjacent to and downstream of the CTO.

There are several different methods that may be employed for locating the CTOs, the area adjacent to and downstream of the CTO and the hybernating and scar myocardium. For example, electrophysiology, electrocardiograms and myocardial perfusion scans can be used to locate damaged cardiac tissue. Other locating methods include, but are not limited to: echocardiography and catheter-based voltage mapping of a portion of the heart; invasive or minimally invasive surgery (visualization of damaged tissue); and other imaging techniques, such as MRI, CAT/64 slice scans, perfusion imaging, fluoroscopy, and angiography. These techniques are know in the art and will not be described here.

The method may further include locating possible connections between the two coronary arteries (i.e., septal perforators and posterior descending artery). For example, simultaneous right and left coronary arteriograms may be performed to show possible connections between the distal left anterior descending coronary artery and posterior descending coronary artery of the right coronary artery. These connections will be utilized to pass a delivery device from one coronary artery to another for delivery of cells though the retrograde approach.

Once the damaged tissue is located and the connections are shown, the donor cells, such as myocytes, stem cells and/or other progenitor cells may then be delivered into the localized area for engraftments into the injured myocardium.

As illustrated in FIGS. 2A-B and 3A-B, if the chronic total occlusion 100 is in the right coronary artery 210, a delivery device may be moved (as shown by arrows) adjacent to the CTO 100 in the coronary artery 210 using either retrograde (FIG. 2A-B) or antegrade (FIG. 3A-B) approach. In both of these approaches, a delivery device 750, such as a microcatheter or catheter may be placed adjacent 510 to the total chronic occlusion 100 using a vascular introducer. The vascular introducer may be inserted into a femoral artery in the groin or radial artery in the wrist to create an insertion point in the femoral artery or the radial artery. For example, a wireguide 600 may be inserted into the femoral artery through the vascular introducer and moved up to and over the aortic arch 90. In an embodiment, the wireguide 600 is a standard wireguide conventionally known and used in the art. A guide catheter or microcatheter 750 may be placed over the wireguide 600 and moved toward the heart (not shown).

Figure 2A:
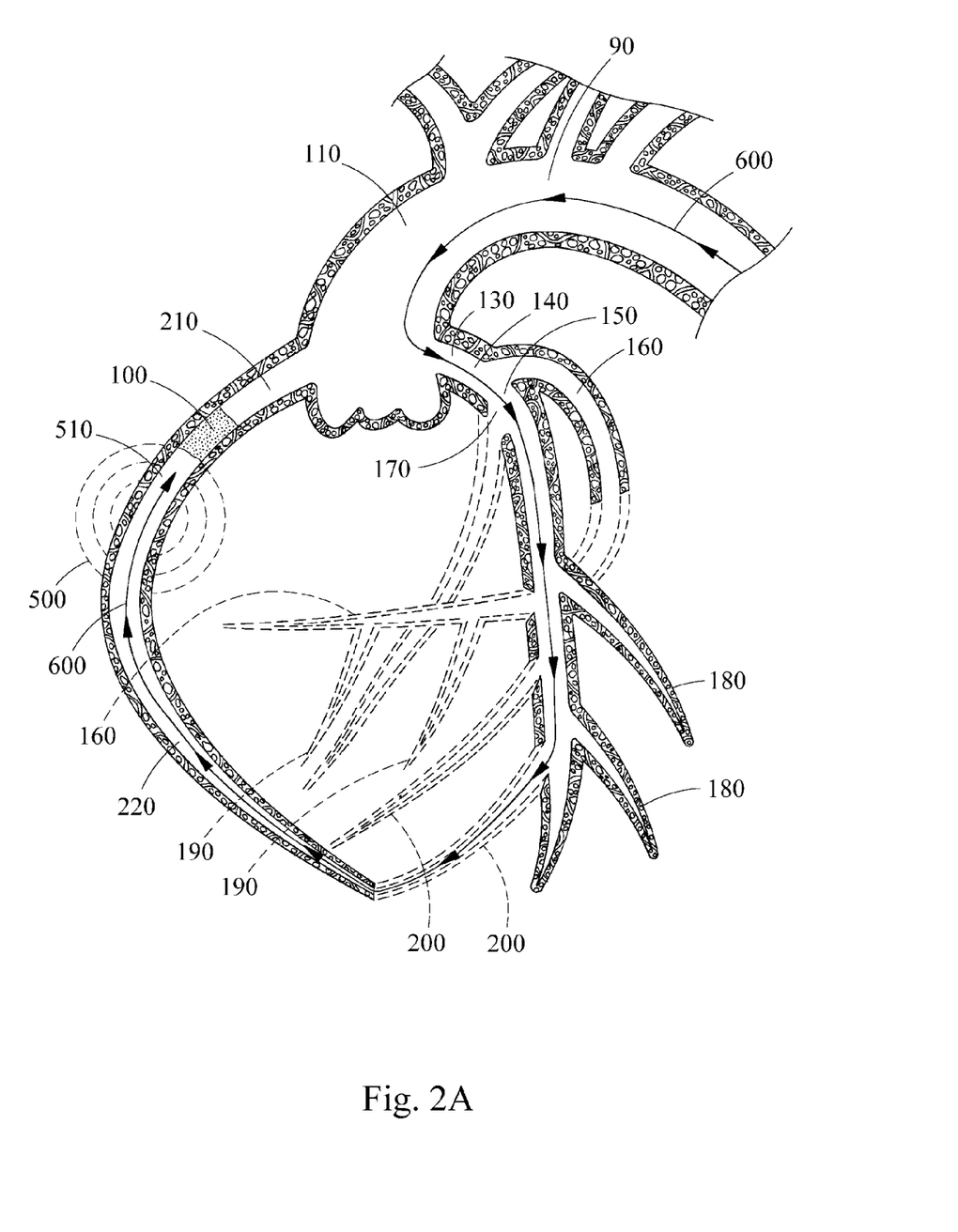
FIGS. 2A-B are schematic illustrations of an embodiment relating to this invention.
Figure 2B:
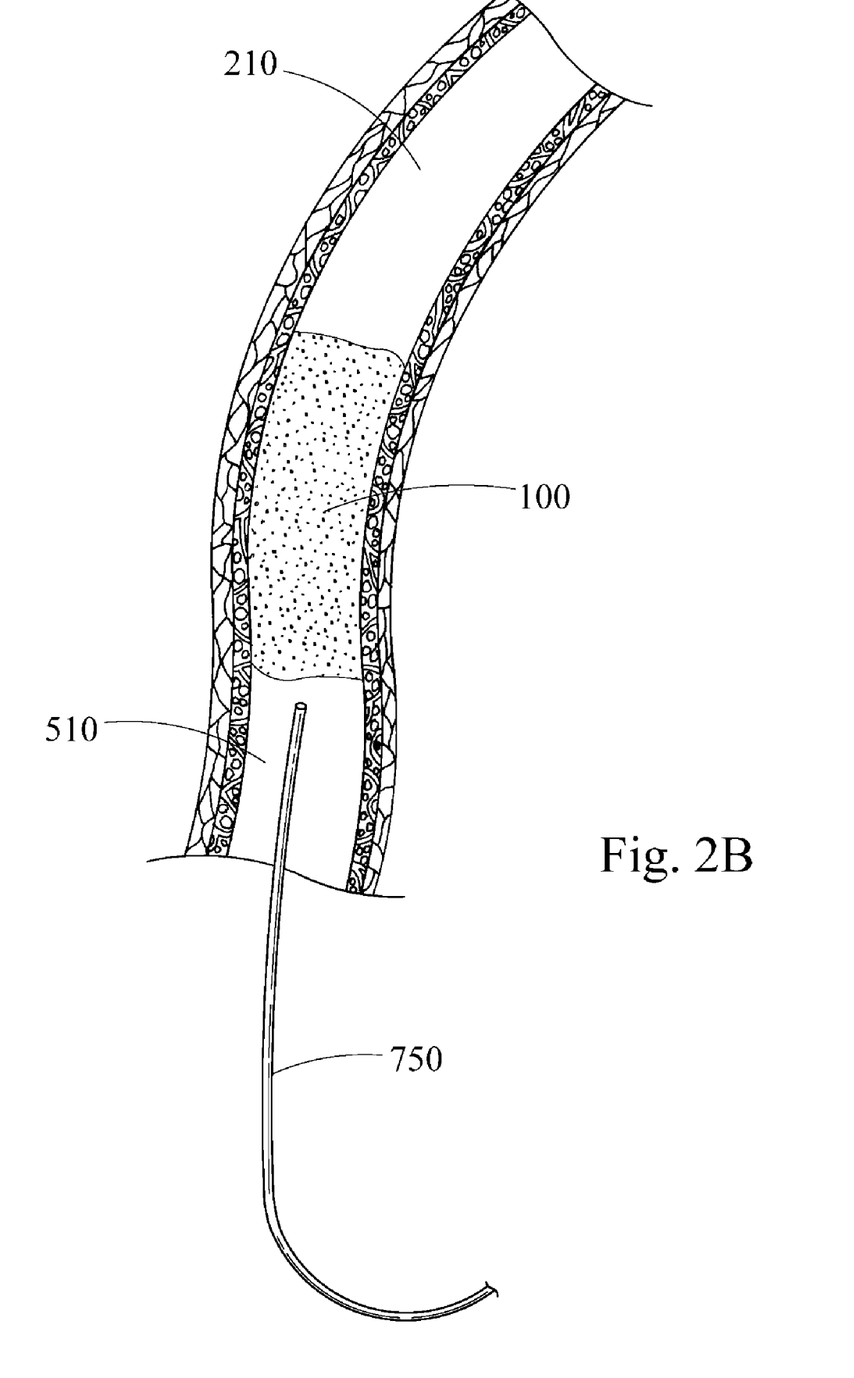

In the retrograde approach, as illustrated in FIG. 2A, the wireguide 600 is moved into the left coronary artery 130 through the left main coronary artery 140, passed into the left anterior descending artery 150 and then into a septal perforator 200 into the posterior descending branch 220 of the right coronary artery 210 and placed adjacent to and downstream 510 of the CTO 100, preferably within about 2 cm from the CTO 100. In FIG. 2A, circumflex coronary artery 160, obtruse marginal branches 190 of the circumflex coronary artery 160, left anterior descending artery 150, first and second septal perforators 200, and diagonal branches 180 of the left anterior descending coronary artery 150 are shown for completion. Zones of viable and non-viable myocardium 510 are also shown. Dotted lines in the figures indicate that the hybernating or scar tissue is located distal to the CTO 100.

Figure 3A:
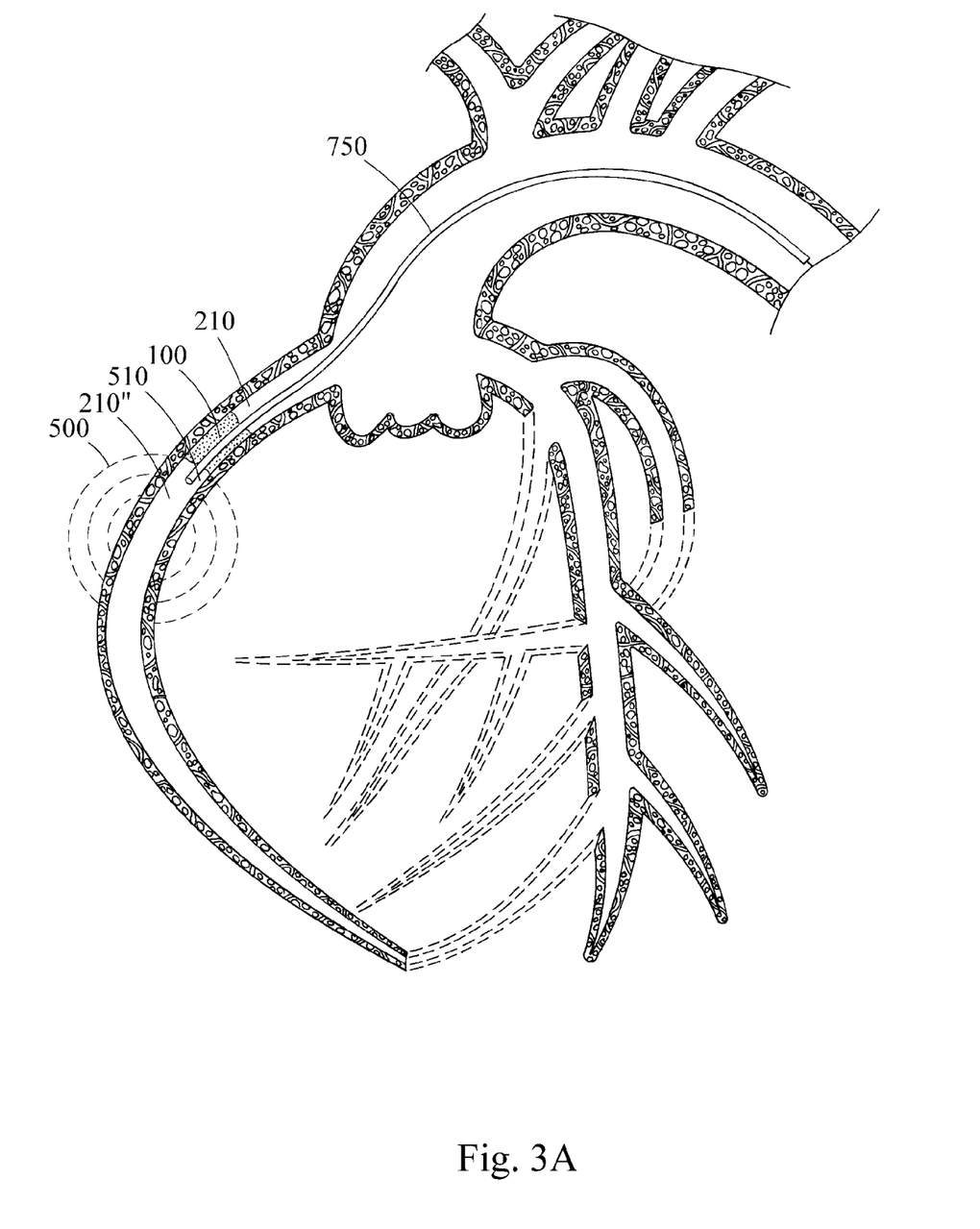
FIGS. 3A-B are also schematic illustrations of another embodiment relating to this invention.
Figure 3B:
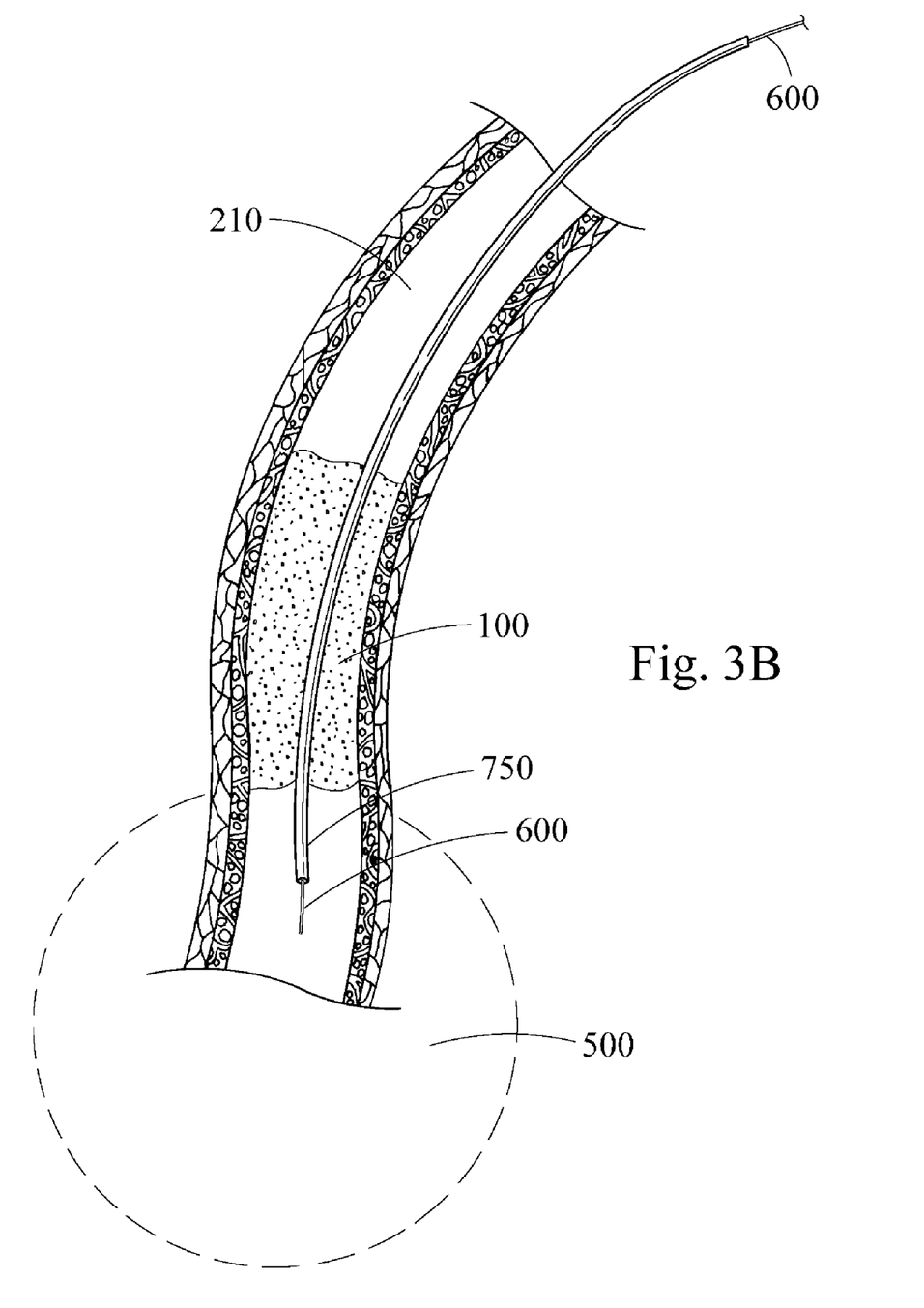

In the antegrade approach illustrated in FIGS. 3A-B, a small antegrade catheter 750 that would create a limited channel for cell injection is moved into the distal right main coronary artery 210" through the CTO 100 though a limited opening (without displacing the occlusion) and placed adjacent to and downstream 510 of the CTO 100, preferably within about 2 cm from the CTO. Alternatively a small opening may be made through the CTO 100 prior to placing a moving the catheter to allow the catheter to pass though the CTO without displacing any of the occluding material. It is important to not displace the CTO so that it continues to provide an area of low flow allowing for longer dwell time for donor cells that are being implanted there. In other words, the CTO functions to prevent the implanted cells from being displaced or washed away from the area by the coronary blood flow. In addition, a biodegradable plug and/or a suture may be used to close the wireguide or the catheter tract through the CTO. Some exemplary biodegradable materials that may be used as a plug include naturally derived collagenous material, such as extracellular matrix (ECM) material, or compositions thereof. ECMs include material such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The hybernating myocardium and associated scar myocardium is shown with 500 in the figure.

As illustrated in FIG. 3B, with a wireguide 600 located adjacent to and downstream of the CTO 100, a microcatheter 750 may be introduced over the wireguide and advanced in the vasculature toward the coronary artery and until the microcatheter is in the area adjacent to and downstream of the CTO 100. An area of hybernating and scar myocardium is shown 500. With the microcatheter 750 in place, the wireguide 600 is removed and a cell delivery device is inserted (not shown) into the vasculature introducer and moved through the lumen of the microcatheter to place the tip of the delivery device at the distal end of the microcatheter. The cell delivery device is preferably flexible allowing it to be deflected, flexed and bent through the tortuous paths of the vasculature to the coronary artery 210. For example, the cells may be delivered by catheter or microcatheter or the like, which are known in the art. Alternatively, any other suitable device may be used.

With the microcatheter in place the donor cells, such as myocytes, stem cells or progenitor cells may be injected to the area adjacent to and downstream of the total chronic occlusion so that the cells are engrafted in the small coronary vessels and capillaries. A biocompatible (e.g., biodegradable) marker may be administered with the donor cells so as to monitor the site(s) of administration of the donor cells and, optionally, later identify the treated region. Since this area would be supplied by collateral circulation only, the flow would be limited and more cells may engraft and establish. Once the cells are delivered, the cell delivery device and the microcatheter are withdrawn from the vasculature, and the cells allowed sufficient time to engraft, divide and establishing themselves (i.e., the engraftment period) at the delivery site, i.e. the site of implantation.

Suitably, the engraftment period is long enough so that the number of cells being delivered at the delivery site has at least doubled, and most preferably, the implantation period is long enough so that the number of cells being delivered at the delivery site has at least tripled. This engraftment period may be anywhere from a few days (for example, 7, 8, 9, 10 days) to a few weeks (for example, about 2 weeks). Preferably, the time period is at least about one week, more preferably, the time period is about two weeks. Other engraftment periods are also contemplated. For example, the engraftment period as long as about 4 weeks or longer.

After the engraftment period, the CTO may be treated by any method know and available in the art to establish increased antegrade flow to the cells to nourish them. In some instances, it may be suitable to determine whether the cells have engrafted and established themselves in the myocardium prior to ablating the CTO. This may be done by performing a perfusion scan. Alternatively, suitable biomarkers may be used. The CTO may be treated by either a retrograde or antegrade approach using methods know in the art. For example, following the incubation in the hybernating myocardium, the CTO may be ablated. Methods and devices that may be used to ablate the chronic total occlusion are known in the art. Some exemplary devices include those previously described in U.S. Pat. Nos. 6,514,217 and 6,719,725; and U.S. Publication Nos. 20040230219 A1; 20050119679 A1; 20060069346 A1; and 20050171478A1, contents of which are incorporated by reference herein in their entireties. Several suitable devices are commercially available from companies such as Cook Medical, Abbott Vascular, Boston Scientific and others.

Once the occlusion is eliminated a patient's heart may be subject to follow up tests, such as stress test or a PET scan to evaluate viability of the heart muscle and patient's heart function.

In some instances, medical devices and/or drug eluting medical devices, such as stents, stent grafts, drug eluting balloons, or drug weeping balloons may be inserted during angioplasty procedure of the CTO.

Either a retrograde (FIG. 4) or antegrade (FIG. 5) approach may be used if the right coronary artery 130 was patent and a CTO 400 of the left anterior descending coronary artery 150 required treatment.

Figure 4:
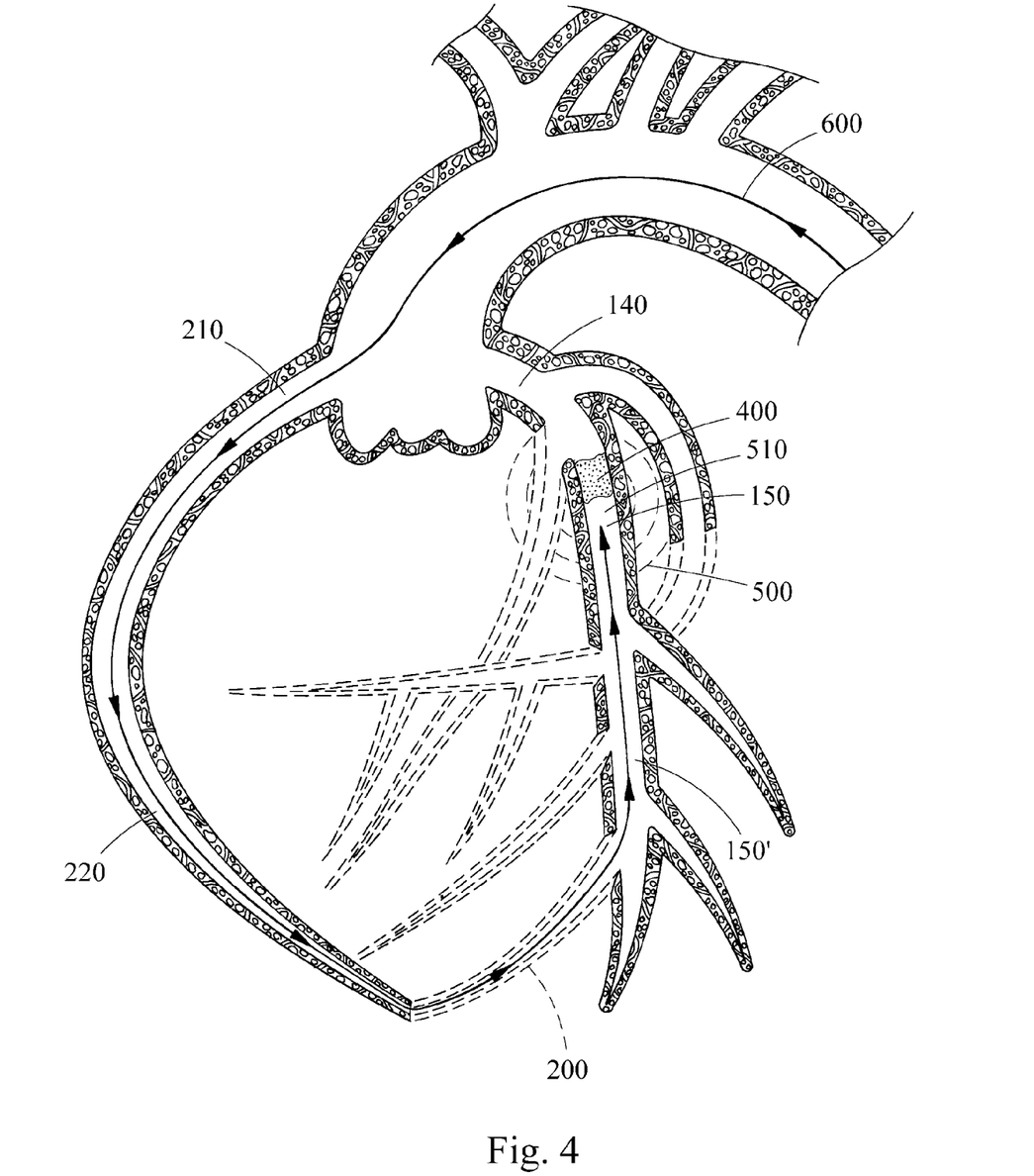
FIG. 4 is yet another schematic illustration of another embodiment relating to this invention.

In the retrograde approach illustrated in FIG. 4, a wireguide 600 is inserted into the right coronary artery 210, to the posterior descending branch 220 of the right coronary artery 210 and through the septal perforator 200 into the distal left anterior descending artery 150' to the left anterior descending coronary artery 150 and to an area adjacent to and just downstream 510 from the CTO 400 of the left anterior descending coronary artery 150 (hybernating and scar myocardium 500). Once in place, a microcatheter (not shown) may be passed over the wireguide 600. With the microcatheter in place, the wireguide 600 may be removed and a delivery device carrying the donor cells, such as myocytes, stem cells or progenitor cells, may be delivered to the area. Once in place, the donor cells may be delivered to the area. The donor cells are preferably delivered so that the small coronary and collateral vessels and capillaries in the area are seeded with the donor cells. Since this area would be supplied by collateral circulation only, the blood flow would be limited and more cells may be engrafted. The CTO 400 may then be treated for example by ablation to establish increased antegrade flow to the cells to nourish them by methods known in the art, some of which were mentioned above.

Figure 5:
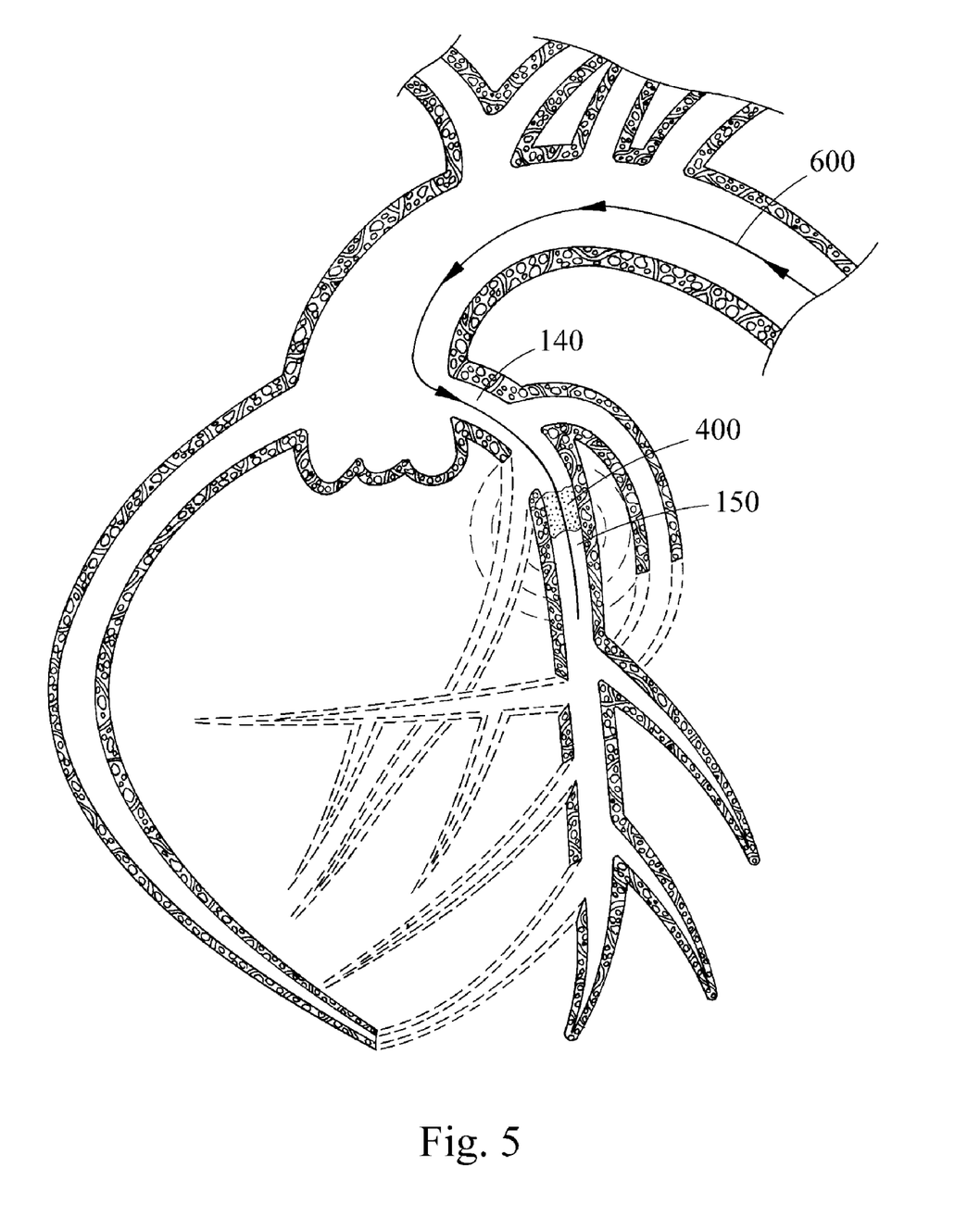
FIG. 5 is also a schematic illustration of further embodiment relating to this invention.

In the antegrade approach illustrated in FIG. 5, the wireguide 600 is moved into the left main coronary artery 140 and to the left anterior descending coronary artery 150 through the CTO 400 without displacing the CTO 400 and placed adjacent to and downstream of the CTO 400. Once in place, a microcatheter (not shown) carrying a delivery device with the donor cells may be delivered and cells injected into the area adjacent to and downstream of the CTO 400.

Following the delivery of the cells using any of the methods described above, the cells are allowed to dwell for a period of time sufficient for the cells to engraft, divide and establish themselves in the hybernating and/or scar myocardium. Preferred engraftment period is long enough so that the number of cells being delivered at the delivery site has at least doubled, and most preferably, the engraftment period is long enough so that the number of cells being delivered at the delivery site has at least tripled.

V. Sources of Donor Cells for Cell-Based Therapy

Sources for donor cells for the cell-based therapy described herein include myocytes, including ventricular myocytes; stem cells (e.g., adult stem cells or embryonic stem cells); or other progenitor cells (e.g., multipotent adult progenitor cells). The donor cell may also include other types of cells, such as skeletal muscle derived cells, skeletal muscle cells, skeletal myoblasts, cardiac derived cells, bone marrow-derived cells, mesenchymal cells, stromal cells, smooth muscle cells, fibroblasts, pluripotent cells, totipotent cells, hematopoietic stem cells, cells from cord blood, and isolated $CD34^+$ cells.

In one embodiment, the donor cells may be autologous cells including xenologous cells, however, non-autologous cells may also be employed. The donor cells can be expanded in vitro to provide an expanded population of donor cells for administration to a recipient animal. In addition, donor cells may be treated in vitro to cause a preferred differentiation. Sources of donor cells and methods of culturing those cells are known in the art. See, for example, U.S. Pat. No. 5,130, 141 and Jain et al. (*Circulation*, 103, 1920 (2001)), wherein the isolation and expansion of myoblasts from skeletal leg muscle is discussed (see also Suzuki et al., *Circulation*, 104, I-207 (2001), Douz et al., *Circulation*, III-210 (2000) and Zimmerman et al., *Circulation Res.*, 90, 223 (2002)). Published U.S. application 2002/0110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,543,318 discusses isolating and culturing human atrial myocytes. U.S. Pat. Nos. 6,090,622 and 6,245,566 discuss preparation of embryonic stem cells, while U.S. Pat. No. 5,486,359 discusses preparation of mesenchymal cells.

The donor cells may also be manipulated in vitro to introduce one or more desirable gene products (transgenes) to the cells. Preferably, the transgenic donor cells include a transgene that enhances cellular proliferation, cellular engraftment, cellular survival, cellular differentiation and/or cellular function of the donor cells in the recipient. The expression of one or more transgenes may be employed to decrease, replace or supplement (increase) the expression of endogenous genes in the donor cells, e.g., if the donor cells are autologous cells and the donor has an inherited or acquired disease associated with aberrant expression of an endogenous gene in cardiac cells. The expression of one or more transgenes may correct the level of the gene product encoded by the transgene in the donor cells. In one embodiment the expression of the transgene is controlled by a regulatable or tissue-specific, e.g., cardiac myocyte-specific promoter. The transgene may be introduced to donor cells by any means including, but not limited to liposomes, electroporation, naked DNA, or viral-mediated transduction, for instance, via adenovirus, adeno-associated virus, retrovirus or lentivirus vectors.

Alternatively, DNA may be delivered to the delivery site adjacent to and downstream of the CTO. Site-specific installation of DNA was previously described in U.S. Pat. Nos. 5,328,470; 5,707,969; 5,698,531; 5,693,622; 6,436,907; and 6,297,220, contents of which are incorporated by reference herein in their entirety.

VI. Cell Compositions and Dosages of the Donor Cells

Pharmaceutical compositions of cells for implantation and treatment of injured myocardium comprise donor cells, including cells from different sources, and optionally at least one agent that enhances donor cell engraftment, survival, proliferation and/or differentiation, enhances cardiac function or stimulate angiogenesis.

The compositions of cells may further optionally include at least one pharmaceutically acceptable excipient, carrier or diluent, which are known in the art.

In certain instances, the composition may be in a liquid form.

The cells to be administered may be a population of individual cells or cells grown in culture so as to form a two dimensional or three dimensional structures. The number of cells to be administered will be an amount which results in a beneficial effect to the recipient, the beneficial effect being for example, enhanced cardiac function. For example, from about $10^2$ to about $10^{10}$, e.g., from about $10^3$ to about $10^9$, about $10^4$ to about $10^8$, about $10^5$ to about $10^7$, about $10^5$ to about $10^{10}$ or cells can be administered to, e.g., injected, the region of interest, for instance, hybernating and scar myocardium. Other amounts are also contemplated.

Agents, which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors, and variants or derivatives thereof, and the like. Such agents may optionally be present in a composition or administered separately.

The cells are administered during a therapeutic vascular procedure or an invasive or minimally invasive surgical procedure. In one embodiment, the cells are administered once the CTO is detected, within hours, e.g., about 0.5 to about 12 hours, to days, e.g., about 1 to about 2 days, and up to about one or more weeks after the CTO is detected. Preferably, the administration of donor cells is prior to scar formation (i.e., prior to formation of scar myocardium). However, cells may also be administered after the scarred tissue has formed. As mentioned before, the scar myocardium may also benefit from cell implantation. The cells may be delivered by a needle, catheter, e.g., a catheter which includes an injection needle or infusion port, or other suitable device, some known in the art.

In one embodiment, skeletal muscle cells may be obtained from a patient. The skeletal muscle cells may be cultured in vitro, e.g., so as to expand the population, or may be employed in the absence of culturing. Prior to cell therapy, the damaged tissue in the patient is located by conventional means, e.g., an electrocardiogram. The autologous donor skeletal muscle cells, prior to administration to the damaged tissue, may be optionally subjected to washing to remove non-cellular components, i.e., components which are not intact cells including components in tissue culture media, and introduced to the damaged tissue in a physiologically compatible carrier (vehicle), e.g., an aqueous, semi-solid or solid vehicle. In one embodiment, approximately $10^2$ to $10^{10}$ donor skeletal muscle cells may be administered via a microcatheter as was described above, which includes an injection needle, plurality of needles, or infusion port, positioned at or near the damaged tissue (hybernating and scar myocardium). A biocompatible (e.g., biodegradable) marker may be administered with the skeletal muscle cells so as to monitor the site(s) of administration of the donor cells and, optionally, later identify the treated region. Once administered, the donor cells develop functional connections with adjacent viable cells, and membrane channels with adjacent viable cells including viable cells in the recipient, and, if not already differentiated, differentiate to myocardial cells.

INDEX OF NUMBERS PRESENT IN THE DRAWINGS

90 Aortic arch
100 Chronic total occlusion in right main coronary artery (RM)
110 Aorta
120 Aortic valve
130 Left coronary artery
130' Left coronary artery cusp
140 Left main coronary artery
150 Left anterior descending coronary artery (LAD)
150' Distal left anterior descending coronary artery
160 Circumflex branch
170 Posterior descending artery
180 Diagonal branches
190 Obtruse marginal branch
200 Septal perforators
210 Right coronary artery
210' Right coronary artery cusp
210" Distal right main coronary artery
220 Posterior descending branch of the right coronary artery
400 Chronic total occlusion in left main coronary artery (LM)
500 Area of hybernating myocardium and scar tissue
510 Area downstream of the chronic total occlusion
600 Guidewire
750 Catheter It is therefore intended that the foregoing detailed description be regarded as illustrative rather than limiting, and that it be understood that it is the following claims, including all equivalents, that are intended to define the spirit and scope of this invention.

The invention claimed is:

1. A method of engrafting donor cells into injured myocardium, comprising:
   delivering via a coronary artery donor cells to a delivery site adjacent to and distal from a chronic total occlusion, wherein the donor cells are capable of creating viable myocardial tissue, and wherein distal from the chronic total occlusion is downstream from the chronic total occlusion,
   allowing the donor cells a time sufficient to engraft, divide, and establish themselves at the delivery site thereby creating viable myocardial tissue at the delivery site; and
   following the delivering and the allowing steps, ablating the chronic total occlusion to establish blood supply to the donor cells.

2. The method of claim 1, wherein the time sufficient to engraft, divide and establish the donor cells at the delivery site is from about 7 days to about 14 days.

3. The method of claim 1, wherein the time sufficient to engraft, divide and establish the donor cells at the delivery site is about 14 days.

4. The method of claim 1, wherein the donor cells are delivered to the delivery site via a delivery device.

5. The method of claim 4, wherein the delivery device is a catheter.

6. The method of claim 4, wherein the delivery device approaches the delivery site through a retrograde approach.

7. The method of claim 4, wherein the delivery device approaches the delivery site through an antegrade approach.

8. The method of claim 4, wherein the delivery device approaches the delivery site through a partial opening of the chronic total occlusion.

9. The method of claim 1, further comprising a step of performing simultaneous right and left coronary arteriograms to show arterial connections.

10. The method of claim 1, wherein the donor cells are myocytes, stem cells or progenitor cells.

11. The method of claim 1, further comprising delivering to the delivery site a composition comprising the donor cells, at least one agent that enhances donor cell engraftment, survival, proliferation and differentiation, and optionally at least one pharmaceutically acceptable excipient, carrier, or diluent.

12. The method of claim 11, wherein the at least one agent is selected from the group consisting of pyruvate, catecholamine stimulating agents, fibroblast growth factor, basic fibroblast growth factor, acidic fibroblast growth factor, fibroblast growth factor-4, fibroblast growth factor-5, epidermal growth factor, platelet-derived growth factor, vascular endothelial growth factor, $VEGF_{121}$, $VEGF_{145}$, $VEGF_{165}$, $VEGF_{189}$ or $VEGF_{206}$, tissue growth factors, variants, and derivatives thereof.

13. The method of claim 11, further comprising delivering a biocompatible marker.

14. The method of claim 1, wherein in the step of delivering, from about $10^2$ to about $10^{10}$ donor cells are delivered.

15. The method of claim 1, wherein the donor cells are delivered about 2 centimeters from the chronic total occlusion.

16. The method of claim 1, further comprising a step of delivering a stent.

17. The method of claim 16, wherein the stent is adapted to deliver at least one pharmaceutical agent to the delivery site.

18. A method of treating injured myocardium comprising
delivering via a coronary artery donor cells to a delivery site adjacent to and distal from a chronic total occlusion, wherein the donor cells are capable of creating viable myocardial tissue, and wherein distal from the chronic total occlusion is downstream from the chronic total occlusion;
allowing the donor cells a time sufficient to engraft, divide, and establish themselves at the delivery site thereby creating viable myocardial tissue at the delivery site; and
following the delivering and the allowing steps, ablating the chronic total occlusion to establish blood supply to the donor cells.

19. A method of engrafting donor cells into injured myocardium, comprising:
delivering via a coronary artery donor cells to a delivery site adjacent to and distal from a chronic total occlusion, wherein the donor cells are capable of creating viable myocardial tissue, and wherein distal from the chronic total occlusion is downstream from the chronic total occlusion;
delivering an agent that enhances donor cell engraftment, survival, proliferation and differentiation;
allowing the donor cells a time sufficient to engraft, divide, and establish themselves at the delivery site thereby creating viable myocardial tissue at the delivery site; and
following the delivering steps and the allowing step, ablating the chronic total occlusion to establish blood supply to the donor cells.

* * * * *